United States Patent
Tjioe (12)

(10) Patent No.: US 6,235,902 B1
(45) Date of Patent: May 22, 2001

(54) METHOD FOR PREPARING MELAMINE

(75) Inventor: Tjay T. Tjioe, Sittard (NL)

(73) Assignee: DSM N.V., Geleen (NL)

( * ) Notice: Subject to any disclaimer, the term of this patent is extended or adjusted under 35 U.S.C. 154(b) by 0 days.

(21) Appl. No.: 09/444,302

(22) Filed: Nov. 22, 1999

Related U.S. Application Data

(63) Continuation of application No. PCT/NL98/00278, filed on May 15, 1998.
(60) Provisional application No. 60/048,476, filed on Jun. 3, 1997.

(30) Foreign Application Priority Data

May 21, 1997 (NL) .................................................. 1006095
Jun. 16, 1997 (EP) .................................................. 97201806

(51) Int. Cl.⁷ ........................ C07D 251/60; C07D 251/62
(52) U.S. Cl. ............................................................ 544/201
(58) Field of Search .............................................. 544/201

(56) References Cited

U.S. PATENT DOCUMENTS

| | | | |
|---|---|---|---|
| 4,465,832 * | 8/1984 | De Wit et al. | 544/201 |
| 4,565,867 | 1/1986 | Thomas et al. | 544/201 |
| 5,514,796 | 5/1996 | Best et al. | 544/201 |
| 5,514,797 | 5/1996 | Best et al. | 544/201 |
| 5,721,363 * | 2/1998 | Canzi et al. | 544/201 |

FOREIGN PATENT DOCUMENTS

| | | |
|---|---|---|
| 0 808 836 | 11/1997 | (EP) . |
| 96/20182 | 7/1996 | (WO) . |
| 96/20183 | 7/1996 | (WO) . |
| 96/23778 | 8/1996 | (WO) . |
| 97/20826 | 6/1997 | (WO) . |
| 97/47609 | 12/1997 | (WO) . |

* cited by examiner

*Primary Examiner*—Richard L. Raymond
*Assistant Examiner*—Venkataraman Balasubramanian
(74) *Attorney, Agent, or Firm*—Pillsbury Winthrop LLP

(57) ABSTRACT

Method for preparing melamine from urea via a high-pressure process in which solid melamine product is obtained directly from the melamine melt by transferring the melamine melt into a product cooling unit where it is cooled with ammonia. The melamine melt from the melamine reactor has a temperature between the melting point of melamine and 450° C. and is sprayed, via spraying means, into a product cooling vessel containing an ammonia environment with an increased pressure, where the melamine melt solidifies to form melamine powder. The melamine powder, having a temperature of between 200° C. and the solidification point of melamine, is maintained under an increased ammonia pressure for a contact time of between 6 seconds and 5 hours at a pressure. During this contact time, the powder melamine product may be maintained in the product cooling vessel, or a series of vessels, at a virtually constant temperature or may be cooled further to a temperature above 200° C.

12 Claims, No Drawings

METHOD FOR PREPARING MELAMINE

This is a continuation of International Application No. PCT/NL98/00278 filed May 15, 1998. This application claims the benefit of U.S. Provisional Application No. 60/048,476, filed Jun. 3, 1997.

The invention relates to a method for preparing melamine from urea via a high-pressure process in which the solid melamine product is obtained by transferring the melamine melt from the reactor into a product-cooling vessel where the melamine melt is cooled with ammonia.

Such a method is disclosed, inter alia, in EP-A-747366 which describes a high-pressure process for preparing melamine from urea. In particular, EP-A-747366 describes how urea is pyrolyzed in a reactor, operating at a pressure of from 10.34 to 24.13 MPa and a temperature of from 354 to 454° C., to produce a reactor product. This reactor product, containing liquid melamine, $CO_2$, and $NH_3$ and is transferred under pressure as a mixed stream to a separator.

In this separator, which is kept at virtually the same pressure and temperature as the reactor, the reactor product is separated into a gaseous stream and a liquid stream. The gaseous stream contains primarily $CO_2$ and $NH_3$ waste gases and a minor component of melamine vapor. The liquid stream mainly comprises a melamine melt. The gaseous stream is transferred to a scrubber unit, while the liquid stream is transferred to a product-cooling unit.

In the scrubber unit, operated at temperature and pressure conditions nearly identical to the reactor conditions, the gaseous stream is scrubbed with molten urea. The heat transfer achieved in the scrubber unit both preheats the molten urea and cools the gaseous stream to a temperature from 177 to 232° C. The molten urea also scrubs the gaseous stream to remove the melamine vapor from the waste gases. The preheated molten urea, along with the melamine that was scrubbed from the $CO_2$ and $NH_3$ waste gases, is then fed into the reactor.

In the product-cooling unit, the melamine melt is cooled and solidified with a liquid cooling medium to produce a solid high purity melamine product without the need for additional purification. The preferred liquid cooling medium is one that forms a gas at the temperature of the melamine melt and at the pressure in the product-cooling unit. EP-A-747366 identifies liquid ammonia as the preferred liquid cooling medium with the pressure in the product-cooling unit being above 41.4 bar. Although according to EP-A-747366 the purity of the solid melamine product obtained using the disclosed process was greater than 99 wt %, this degree of purity has proven difficult to maintain continuously on a commercial scale. The inability to maintain a purity greater than 99 wt % is a drawback that renders the melamine produced less suitable for more demanding applications, particularly melamine-formaldehyde resins used in laminates and/or coatings.

It is the object of the present invention to provide an improved method for preparing melamine from urea, in which high purity melamine may be consistently obtained as a dry powder directly from the reactor product. More particularly, the object of the present invention is to provide an improved high-pressure process for preparing melamine from urea, in which high purity melamine obtained as a dry powder directly from the melamine melt by cooling the melamine melt with a liquid cooling medium.

We have found that high purity melamine can be continuously produced directly from the melamine melt coming from the separator. The melamine melt, which has a temperature between the melting point of melamine and about 450° C., is sprayed via spraying means into a solidification vessel. An ammonia atmosphere is maintained in the solidification vessel with the pressure of the ammonia being above 1 MPa, preferably above 1.5 Mpa, more preferably above 4.5 Mpa and even more preferably above 6 Mpa. The upper limit of the pressure of the amonia is below 40 Mpa, preferably below 25 Mpa and more preferably below 11 Mpa. As it enters the solidification vessel the melamine melt is cooled and solidified by contact with the liquid and gaseous ammonia to produce melamine powder having a temperature of between 200° C. and the solidification point of melamine, preferably between 240° C. and the solidification point, and most preferably between 270° C. and the solidification point. Once solidified, the melamine powder is maintained under ammonia pressure for a contact time of between 6 seconds and 5 hours, preferably between 30 seconds and 2 hours.

During this contact time, the temperature of the melamine product can remain virtually constant or it may be cooled to a temperature above 200° C., preferably above 240° C., or, most preferably, above 270° C., over a period of between 6 seconds and 5 hours, preferably over a period of between 30 seconds and 2 hours. The melamine product may be cooled in the solidification vessel or in a separate cooling vessel.

The advantage of the method according to the present invention is the continuous production, on a commercial scale, of dry melamine powder with a purity above 99 wt %. The high purity melamine produced according to the present invention is suitable for virtually any melamine application, including melamine-formaldehyde resins used in laminates and/or coatings.

The preparation of melamine preferably uses urea as the raw material, the urea being fed into the reactor as a melt and reacted at elevated temperature and pressure. Urea reacts to form melamine, and the by-products $NH_3$ and $CO_2$, according to the following reaction equation:

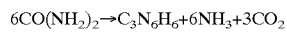

$$6CO(NH_2)_2 \rightarrow C_3N_6H_6 + 6NH_3 + 3CO_2$$

The production of melamine from urea can be carried out at high pressure, preferably between 5 and 25 MPa, without the presence of a catalyst, at reaction temperatures between 325 and 450° C., and preferably between 350 and 425° C. The by-products $NH_3$ and $CO_2$ are usually recycled to an adjoining urea factory.

The above-mentioned objective of the invention is achieved by employing an apparatus suitable for the preparation of melamine from urea. An apparatus suitable for the present invention may comprise a scrubber unit, a reactor having either an integrated gas/liquid separator or a separate gas/liquid separator, possibly a post-reactor, a first cooling vessel, and possibly a second cooling vessel. When a separate gas/liquid separator is used, the pressure and temperature of the separator are virtually identical to the temperature and pressure in the reactor.

In an embodiment of the invention, melamine is prepared from urea in an apparatus comprising a scrubber unit, a melamine reactor having either an integrated gas/liquid separator or a separate gas/liquid separator, a first cooling vessel, and a second cooling vessel. In this embodiment, the urea melt is fed into a scrubber unit operating at a pressure of from 5 to 25 MPa, preferably from 8 to 20 MPa, and at a temperature above the melting point of urea. This scrubber unit may be provided with a cooling jacket or internal cooling bodies to provide additional temperature control.

As it passes through the scrubber unit, the urea melt contacts the reaction waste gases coming from the melamine reactor or the separate gas/liquid separator. The reaction gases mainly consist of $CO_2$ and $NH_3$ and may include a minor amount of melamine vapor. The urea melt scrubs the melamine vapor from the $CO_2$ and $NH_3$ waste gases and carries this melamine along back to the reactor. In the scrubbing process, the waste gases are cooled from the temperature of the reactor, i.e. from 350 to 425° C., to from 170 to 240° C., the urea being heated to from 170 to 240° C. The $CO_2$ and $NH_3$ waste gases are removed from the top of the scrubber unit and may, for example, be recycled to an adjoining urea factory, where they can be used as raw materials for the urea production.

The preheated urea melt is drawn off from the scrubber unit, together with the melamine scrubbed from the waste gases, and transferred to the high pressure reactor operating at pressures between 5 and 25 MPa, and preferably between 8 and 20 MPa. This transfer may be achieved using a high-pressure pump or, where the scrubber is positioned above the reactor, gravity, or a combination of gravity and pumps.

In the reactor, the urea melt is heated to a temperature between 325 and 450° C., preferably between about 350 and 425° C., under a pressure between 5 and 25 MPa, preferably between 8 and 20 MPa, to convert the urea into melamine, $CO_2$, and $NH_3$. In addition to the urea melt, a certain amount of ammonia can be metered into the reactor as, for example, a liquid or hot vapor. The additional ammonia, although optional, may serve, for example, to prevent the formation of condensation products of melamine such as melam, melem, and melon, or to promote mixing in the reactor. The amount of additional ammonia supplied to the reactor may be up to 10 moles ammonia per mole of urea, preferably up to 5 moles ammonia per mole of urea, and, most preferably, up to 2 moles of ammonia per mole of urea.

The $CO_2$ and $NH_3$ produced in the reaction, as well as any additional ammonia supplied, collect in the separation section, for example in the top of the reactor or in a separate gas/liquid separator positioned downstream of the reactor, and are separated from the liquid melamine. If a separate, downstream gas/liquid separator is used, it may be advantageous for additional ammonia to be metered into this separator. The amount of ammonia in this case is 0.01–10 moles of ammonia per mole of melamine, and preferably 0.1–5 moles of ammonia per mole of melamine. Adding additional ammonia to the separator promotes the rapid separation of carbon dioxide from the reactor product, thus preventing the formation of oxygen-containing by-products. As described above, the gas mixture removed from the gas/liquid separator may be passed to the scrubber unit in order to remove melamine vapor and preheat the urea melt.

The melamine melt, having a temperature between the melting point of melamine and 450° C., is drawn off from the reactor or from the downstream gas/liquid separator and sprayed into a cooling vessel to obtain the solid melamine product. Prior to spraying, however, the melamine melt may be cooled from the reactor temperature to a temperature closer to, but still above, the melting point of melamine.

The melamine melt will be drawn off from the reactor at a temperature preferably above 390° C., and more preferably above 400° C., and will be cooled at least 5° C., and preferably at least 15° C., before spraying into the cooling vessel. Most preferably the melamine melt will be cooled to a temperature that is 5–20° C. above the solidification point of melamine. The melamine melt may be cooled in the gas/liquid separator or in a separate apparatus downstream of the gas/liquid separator. Cooling can take place by injection of a cooling medium, for example ammonia gas having a temperature below the temperature of the melamine melt, or by passing the melamine melt through a heat exchanger.

Furthermore, ammonia can be introduced into the melamine melt in such a way that a gas/liquid mixture is sprayed in the spraying means. In this case, the ammonia is introduced at a pressure above that of the melamine melt and preferably at a pressure between 15 and 45 MPa.

The residence time of the melamine melt between the reactor and the spraying means is preferably at least 10 minutes, and most preferably at least 30 minutes, and usually less than 4 hours.

The melamine melt, possibly together with ammonia gas, is transferred to a spraying means where it is sprayed into a first cooling vessel to solidify the melamine melt at increased pressure and form a dry melamine powder. The melamine powder thus formed having a temperature between 200° C. and the solidification point of melamine, preferably between 240° C. and the solidification point, and most preferably between 270° C. and the solidification point. At increased pressure means at a pressure above 1 Mpa, preferably above 1.5 Mpa, more preferably above 4.5 Mpa and even more preferably above 6 Mpa. The upper limit of the ammonia pressure is below 40 Mpa, preferably below 25 Mpa and more preferably below 11 MPa.

The melamine powder is then held under ammonia pressure for a contact time period between 6 seconds and 5 hours, and preferably for a period between 30 seconds and 2 hours. During this contact time, the melamine powder may be maintained at temperature or may be cooled further to a temperature above 200° C., preferably above 240° C., and most preferably above 270° C., over a period of between 6 seconds and 5 hours, preferably over a period of between 30 seconds and 2 hours. If desired, this additional cooling may take place in the first cooling vessel or in a separate second cooling vessel.

The invention will be explained in more detail with reference to the following example.

EXAMPLE

Melamine melt having a temperature of 402° C. was introduced, via a spraying device, into a high-pressure vessel and cooled with liquid ammonia that is simultaneously being sprayed into the vessel. The temperature in the vessel is 296° C. and the ammonia pressure varies between 6.8 and 9.2 MPa. After 2 minutes the melamine powder is cooled to ambient temperature. The end product contained 0.5 wt % of melam and less than 0.2 wt % of melem.

Comparative Example

Melamine melt of 400° C., held in a tube under an ammonia pressure of 13.6 MPa, was rapidly cooled to ambient temperature by contacting the closed tube with a mixture of ice and water. The end product contains 1.4 wt % of melam and 0.4 wt % of melem.

What is claimed is:

1. A method for preparing melamine from urea via a high-pressure process in which solid melamine is obtained by the melamine melt coming from the reactor being transferred to a vessel where the melamine melt is cooled with ammonia, wherein the melamine melt coming from the reactor has a temperature between the melting point of melamine and 450° C. and is sprayed via a spraying means within a first vessel, the first vessel containing an ammonia environment at a pressure of above 1 MPa;

the melamine melt being converted into melamine powder having an initial temperature between 200° C. and the solidification point of melamine, the difference between the initial temperature and 200° C. defining a maximum cooling range, the melamine powder being maintained in the first vessel, or in a plurality of vessels including the first vessel, under an ammonia environment for a contact period, the contact period being between 6 seconds and 5 hours at a pressure of at least 1 MPa with the temperature of the melamine powder at the end of the contact period defining a final temperature, the final temperature being above 200° C., and the difference between the initial temperature and the final temperature being between 0° C. and the maximum cooling range; and.

2. A method according to claim 1 wherein the melamine melt is converted into melamine powder having an initial temperature between 240° C. and the solidification point of melamine.

3. A method according to claim 1 wherein the melamine melt is converted into melamine powder having an initial temperature between 270° C. and the solidification point of melamine.

4. A method according to claims 1, 2, or 3 wherein the melamine powder maintained under an ammonia environment for a contact period of between 30 seconds and 2 hours.

5. A method according to claims 2 or 3 wherein the melamine powder has a final temperature above 240° C. and the difference between the initial temperature and 240° C. defines the maximum cooling range.

6. A method according to claim 3 wherein the melamine powder has a final temperature above 270° C. and the difference between the initial temperature and 270° C. defines the maximum cooling range.

7. A method according to claims 2 or 3 wherein the product has a final temperature above 240° C., the difference between the initial temperature and 240° C. defining the maximum cooling range, and a contact period of between 30 seconds and 2 hours.

8. A method according to claim 3 wherein the product has a final temperature above 270° C., the difference between the initial temperature and 270° C. defining the maximum cooling range, and a contact period of between 30 seconds and 2 hours.

9. A method according to claim 3 wherein the melamine powder has a final temperature above 240° C. and a contact period of between 6 seconds and 5 hours.

10. A method according to claim 9, wherein the melamine product has a final temperature above 270° C. and a contact period of between 6 seconds and 5 hours.

11. A method according to claim 2 or 3, wherein the melamine powder has a final temperature above 240° C. and a contact period of between 30 seconds and 2 hours.

12. A method according to claim 3, wherein the melamine powder has a final temperature above 270° C. and a contact period of between 30 seconds and 2 hours.

* * * * *

UNITED STATES PATENT AND TRADEMARK OFFICE
CERTIFICATE OF CORRECTION

PATENT NO.    : 6,235,902 B1
DATED         : May 22, 2001
INVENTOR(S)   : Tjioe, Tjay, T.

It is certified that error appears in the above-identified patent and that said Letters Patent is hereby corrected as shown below:

Claim 1,
Should read as follows:

1. A method for preparing melamine from urea via a high-pressure process in which solid melamine is obtained by the melamine melt coming from the reactor being transferred to a vessel where the melamine melt is cooled with ammonia, wherein the melamine melt coming from the reactor has a temperature between the melting point of melamine and 450° C. and is sprayed via a spraying means within a first vessel, the first vessel containing an ammonia environment at a pressure of above 1 MPa;

the melamine melt being converted into melamine powder having an initial temperature between 200° C. and the solidification point of melamine, the difference between the initial temperature and 200° C. defining a maximum cooling range, the melamine powder being maintained in the first vessel, or in a plurality of vessels including the first vessel, under an ammonia environment for a contact period, the contact period being between 6 seconds and 5 hours at a pressure of at least 1 MPa with the temperature of the melamine powder at the end of the contact period defining a final temperature, the final temperature being above 200° C., and the difference between the initial temperature and the final temperature being between 0° C. and the maximum cooling range[; and].

Signed and Sealed this

Sixteenth Day of April, 2002

*Attest:*

*Attesting Officer*

JAMES E. ROGAN
*Director of the United States Patent and Trademark Office*